United States Patent [19]

Erpicum et al.

[11] Patent Number: 4,505,706
[45] Date of Patent: Mar. 19, 1985

[54] DISPOSABLE ADULT DIAPER

[75] Inventors: Emile Erpicum, Pont-a-Celles; Louis Dehan, Neupre, both of Belgium

[73] Assignee: Colgate-Palmolive Company, New York, N.Y.

[21] Appl. No.: 457,860

[22] Filed: Jan. 14, 1983

[51] Int. Cl.$^3$ ............................................. A61F 13/16
[52] U.S. Cl. .................................. 604/389; 604/374
[58] Field of Search ............... 604/385, 379, 386, 387, 604/367, 374

[56] References Cited

U.S. PATENT DOCUMENTS

| | | | |
|---|---|---|---|
| 3,672,371 | 6/1972 | Roeder | 604/387 |
| 3,731,688 | 5/1973 | Litt et al. | 604/385 |
| 4,057,061 | 11/1977 | Ishikawa et al. | 604/379 |

Primary Examiner—John D. Yasko
Attorney, Agent, or Firm—Herbert S. Sylvester; Murray M. Grill; Norman Blumenkopf

[57] ABSTRACT

A disposable adult diaper comprising a waterproof backing sheet, an absorbent pad assembly, and a nonwoven hydrophobic top sheet. The top sheet overlies the absorbent pad assembly and is folded about the backing sheet with end margins overlapping. On the overlapped portion of the top sheet there is provided pressure-sensitive adhesive for removably attaching the diaper to an undergarment of the wearer. The diaper is folded into a box-pleated configuration for better fluid tightness and fluid capacity. The absorbent pad assembly may be made with or without top or bottom wadding sheets and the most preferable embodiment utilizes a bottom wadding sheet integrated to the wood fluff of the absorbent pad by a water spray.

4 Claims, 7 Drawing Figures

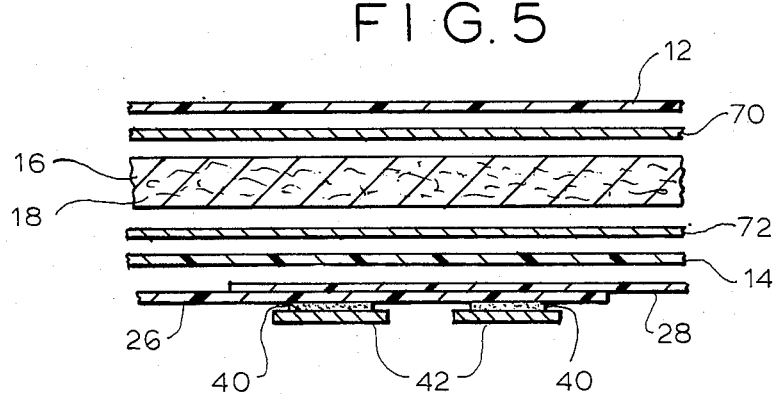
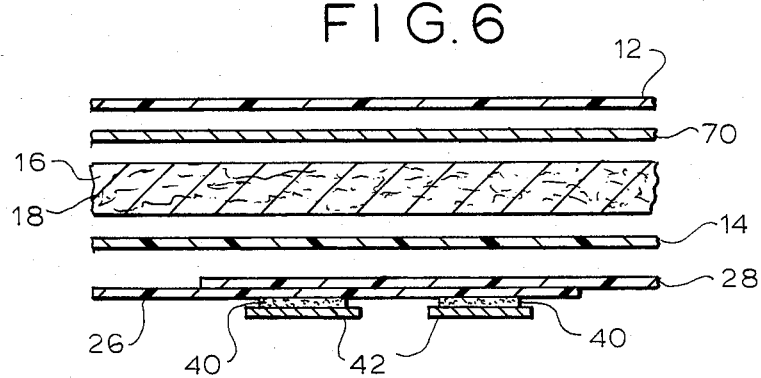
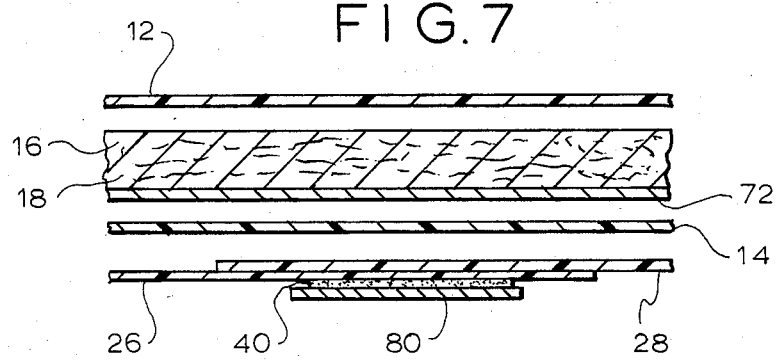

DISPOSABLE ADULT DIAPER

BACKGROUND OF THE INVENTION

1. Field of the Invention

This invention relates to disposable absorbent articles and, more particularly, to a convenient disposable adult diaper.

2. State of the Prior Art

A great many disposable absorbent articles, especially disposable diapers have been previously devised. The disposable diaper now being marketed is characterized by havin a backing sheet, a top sheet and an absorbent pad assembly sandwiched therebetween. The backing sheet is made of a waterproof plastic film, the top sheet may be of tissue or other material but by far the most mass produced is non-woven hydrophobic material. The absorbent pas assembly is made from a variety of absorbent materials and the well-known "wood fluff" has proven highly marketable.

In assembling the prior art diaper, the backing sheet is generally folded over and above the top sheet along two opposite peripheral edges thereof while the other two peripheral edges are bonded together by any suitable means, such as adhesives, or sonic or heat welding. The prior art diapers may be flat, box-pleated or contoured, with or without elasticized waist or crotch bands.

In addition, various types of diapers have been used for adults, especially those persons who are incontinent due to mental or emotional problems, as well as physical illnesses including bladder or urinary disorders, postate involvement or senility. Persons having these problems can have useful lives if embarrassment is avoided by employing an adult diaper capable of being comfortably employed with conventional clothing. However, the backing sheet employed in prior art diapers when directly contacting the conventional undergarments of the wearer may pull away from pressure-sensitive adhesive applied thereon, and often makes a crinkling or like sound upon movement of the wearer, which is likely to cause discomfort or embarrassment.

SUMMARY OF THE INVENTION

The present invention overcomes the problems of prior art diapers by providing a convenient and safe disposable adult diaper which is capable of absorbing a substantial quantity of fluid, has box-pleated panels forming fluid traps to entrap sudden gushes of fluid, and has a top sheet folded beneath the backing sheet to provide means for applying pressure-sensitive adhesive which will not pull away from the diaper while preventing crinkling or other distrubing sounds from the diaper upon movement of the wearer.

The disposable adult diaper according to the present invention includes a backing sheet of waterproof plastic film, an absorbent pad assembly, and a top sheet bonded to the backing sheet along two peripheral edges and which has two ends folded under and about the backing sheet to provide an overlap on which pressure-sensitive adhesive strips are coated and removably covered by strips of material having a low affinity for the adhesive strips. The adult diaper is box pleated forming security seals against fluid loss. Since the overlapping ends of the top sheet are bonded to the backing sheet and each other, they form a better base for attachment to the undergarment. Further, the adhesive utilized has greater affinity for the top sheet material than for undergarmet material preventing tacky residue remaining on the undergarment.

BRIEF DESCRIPTION OF THE DRAWINGS

FIG. 5 is an exploded partial sectional view of an embodiment of the diaper having top and bottom wadding sheets;

FIG. 6 is a view similar to FIG. 5 of another form of the invention employing no bottom wadding sheet; and, FIG. 7 is a view, similar to FIG. 5, of a most preferred embodiment employing an integrated core and wadding sheet.

DETAILED DESCRIPTION OF THE INVENTION

Figure 1:
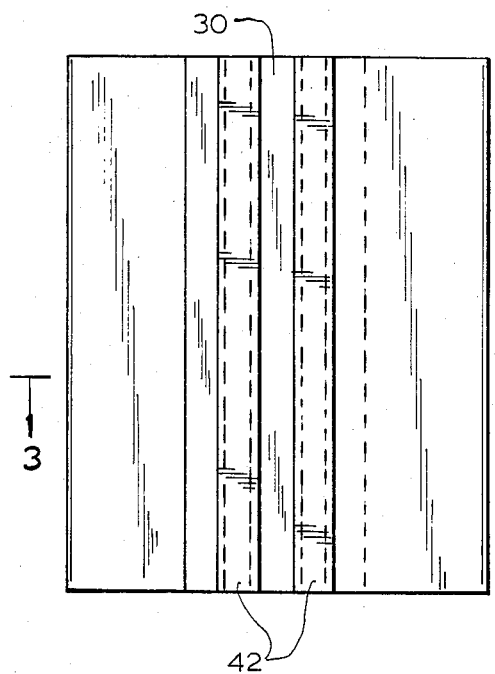
FIG. 1 is a bottom plan view of the adult diaper in a flat state.
Figure 3:
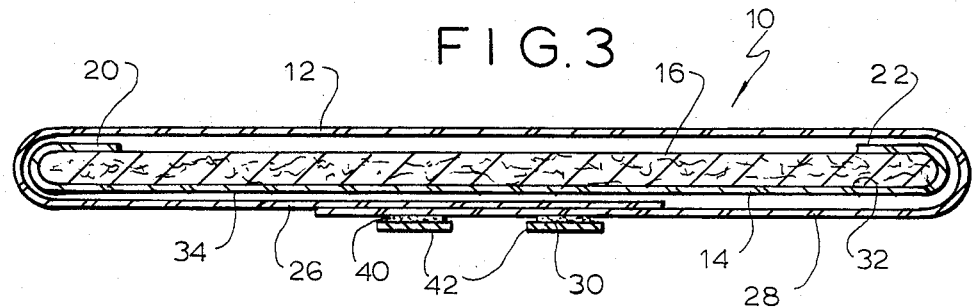
FIG. 3 is a vertical sectional view of the diaper taken along line 3—3 in FIG. 1 and turned to the top sheet uppermost.

With continuing reference to the drawings and initial attention to FIGS. 1 and 3, reference numeral 10 generally designates an adult diaper constructed in accordance with the concepts of the invention. The diaper 10 is preferably of a generally rectangular shape and includes a top sheet 12, a backing sheet 14, and an absorbent pad assembly which, in the embodiment shown, is a core 18 of wood fluff or similar mass produced absorbent material.

The backing sheet 14 is a film of fluid impervious waterproof plastic material, such as polyethylene or polypropylene, and has side portions 20, 22 folded over and overlying the pad assembly 16 since it is of greater outside dimensions.

The top sheet is a tissue sheet of non-woven hydrophobic fibers of polyethylene or polypropylene or a combination thereof. The sheet 12 is much wider than the bottom sheet and is folded under to form end portions 26, 28, which underlie the bottom sheet 14 and form an overlap 30.

The backing sheet 14 is provided with glue lines of any suitable adhesive, such as hot melt or cold setting adhesives, on both sides of the backing sheet so as to bond the absorbent pad assembly thereto. The glue lines extend over the entire upper face 32 of the backing sheet 14 so that the end portions 20, 22 are also bonded to the absorbent pad assembly 16.

The glue lines extend along the bottom surface of the underside 34 of the backing sheet 14 to bond the end portions 26 and 28 of the top sheet thereto. The end portions 26, 28 are bonded to each other at the overlap 30. At the opposed edges at top and bottom of the diaper, the top sheet 12 and the bottom sheet 14 are sealed together as by bonding using adhesives, using crossed glue lines, by heating sealing, sonic welding or other suitable bonding means.

Applied on the undersurface of the overlap 30 are pressure-sensitive adhesive strips 40, which are covered by peelable strips 42. The strips are removed when the diaper is used to fix the diaper to an undergarment of the wearer.

Figure 2:
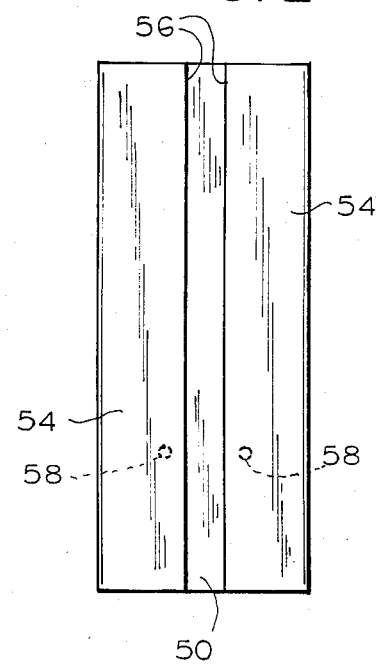
FIG. 2 is a top plan view of the adult diaper shown in box-pleated configuration.
Figure 4:
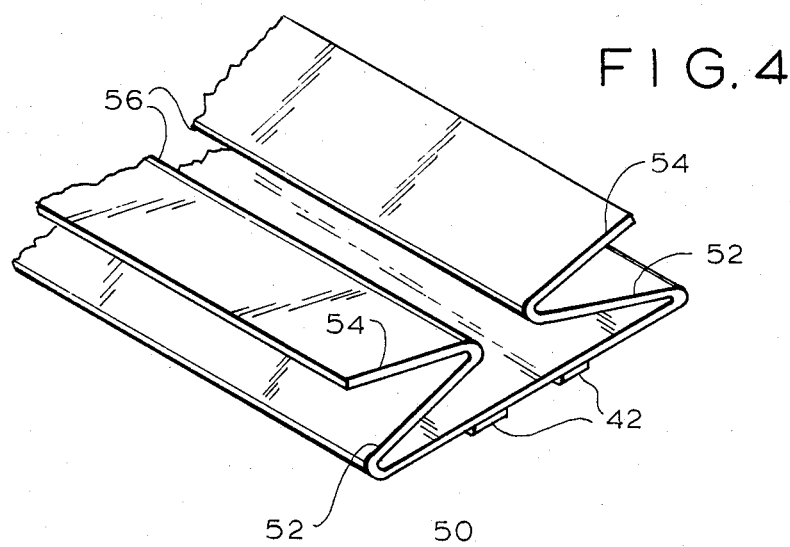
FIG. 4 is a perspective view of the diaper in box-pleated configuration.

The diaper 10, as shown in FIGS. 2 and 4, is folded into a box-pleated configuration, including a base panel 50, inwardly extending panels 52 and outwardly bent wing panels 54. The edges 56 defined by the wind panels 54 as they are bent away from the panels 52 are well spaced from each other. Glue spots 58 are used to hold the panels 52 to the base panel 50 so that the box-pleated configuration forms a suitable fluid seals. The glue spots 58 are slightly offset from the center line of the daiper so that the diaper is equally useful for both male and female wearers.

In the embodiment shown in FIG. 5, the absorbent pad assembly 16 includes a core 18 of wood fluff and an upper wadding sheet 70 and lower wadding sheet 72. The wadding sheets 70, 72 may be in the form of a single piece wrapped about the core 18.

In the form of the invention shown in FIG. 6, only an upper wadding sheet 70 is employed, the core 18 being bonded to the backing sheet 14.

Referring now to the most preferred embodiment shown in FIG. 7, a bottom wadding sheet 72 has been integrated to the core 18 by a water spray so that the bottom wadding sheet 72 is integrally a part of the core 18. As shown, only a single peelable strip 80 may be employed in lieu of the separate peelable strips 42.

What is claimed is:

1. A disposable adult diaper arranged in a box-pleated configuration, comprising a top sheet, a fluid impervious backing sheet and an absorbent pad assembly sandwiched between said top sheet and said backing sheet, said absorbent pad assembly including a core of wood fluff and a bottom wadding sheet integrally bonded to said wood fluff, said core being bonded to said backing sheet, said top sheet being of a non-woven hydrophobic material and being of much greater width than said backing sheet so that end portions of said top sheet underlie said backing sheet and overlap each other, means bonding said end portions to said backing sheet and to each other at said overlap, pressure-sensitive adhesive strips on said overlap, and peelable strip means removably overlying said strips whereby said strips are centrally exposed by said box-pleated configuration.

2. A disposable adult diaper according to claim 1, wherein said backing sheet has side portions folded over said absorbent pad assembly and bonded thereto.

3. A disposable adult diaper according to claim 1, wherein said absorbent pad assembly includes an upper wadding sheet.

4. A disposable adult diaper according to claim 1, wherein said absorbent pad assembly includes a sheet wrapped thereabout forming upper and said lower wadding sheets.

* * * * *